United States Patent [19]

Dangelmaier et al.

[11] Patent Number: 5,796,015

[45] Date of Patent: Aug. 18, 1998

[54] APPARATUS FOR TAKING A VOLUME-ADJUSTABLE SAMPLE FROM A MOVING FLUID

[75] Inventors: Peter Dangelmaier, Wiggensbach; Martin Steiger, Pfronten-Weissbach, both of Germany

[73] Assignee: Endress+Hauser Wetzer GmbH+Co. KG, Nesselwang, Germany

[21] Appl. No.: 761,384

[22] Filed: Dec. 6, 1996

[30] Foreign Application Priority Data

Dec. 11, 1995 [EP] European Pat. Off. ............ 95710019

[51] Int. Cl.$^6$ .................................................. G01N 1/20
[52] U.S. Cl. ........................... 73/863.56; 73/863.57
[58] Field of Search ................. 73/863.03, 863.56, 73/863.57

[56] References Cited

U.S. PATENT DOCUMENTS

| 3,217,548 | 11/1965 | Cordell et al. ............. 73/863.57 |
|---|---|---|
| 3,595,087 | 7/1971 | Starks ..................... 73/863.56 X |
| 3,769,841 | 11/1973 | Thulin . |
| 3,798,972 | 3/1974 | Collins, Jr. . |
| 3,940,993 | 3/1976 | Lapidot . |
| 3,994,170 | 11/1976 | Czarnecki . |
| 4,022,059 | 5/1977 | Schontzler et al. .................. 73/198 |
| 4,574,645 | 3/1986 | Allen et al. .................. 73/863.56 X |
| 5,398,557 | 3/1995 | Shimizu et al. ................ 73/863.57 X |

FOREIGN PATENT DOCUMENTS

| 3803352 | 8/1989 | Germany ................ 73/863.56 |
|---|---|---|
| 424038 | 4/1974 | U.S.S.R. ................. 73/863.57 |
| WO 94/23564 | 10/1994 | WIPO . |

*Primary Examiner*—Thomas P. Noland
*Attorney, Agent, or Firm*—Bose McKinney & Evans

[57] ABSTRACT

This apparatus (10) serves for taking a volume-adjustable sample from a fluid moving in an open channel or flowing in an unpressurized state in a pipe. The apparatus has a chamber (11) for receiving the sample and an intake/discharge line (12) which is immersed in the fluid and is connected to an opening (13) in a base (14) of the chamber. A sample outlet line (15) is arranged in the base of the chamber. The intake/discharge line opens into a vertical inner intake pipe (16). A a rotatable outer intake pipe (17) is placed over the inner intake pipe (16). The wall of the inner intake pipe (16) is provided with an axially parallel elongate hole (161) and the wall of the outer intake pipe (17) is provided with a helical elongate hole (171) extending over a rotational angle of less than 360°, or vice versa. The outer intake pipe is turned by a rotary actuator.

2 Claims, 2 Drawing Sheets

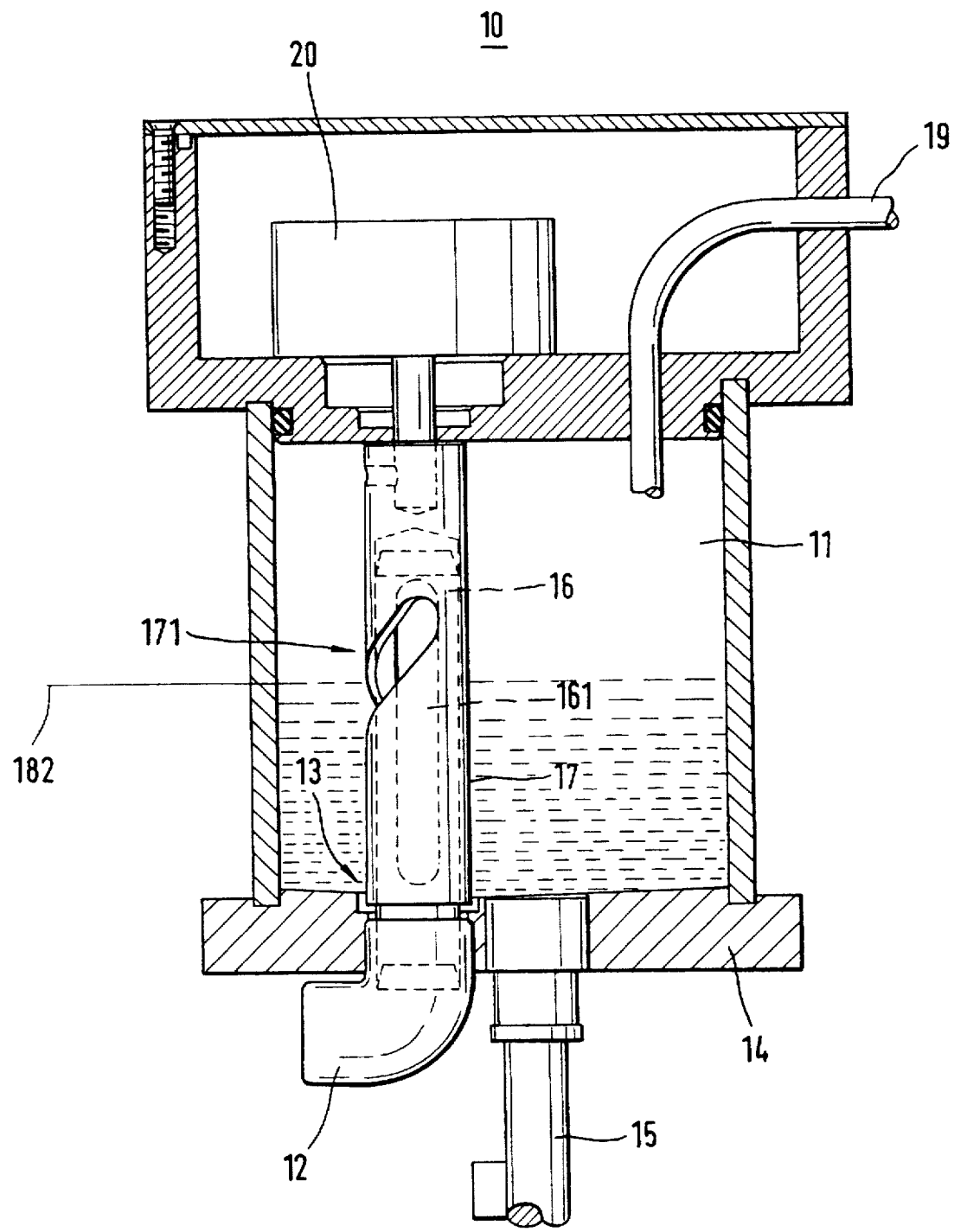

5,796,015

APPARATUS FOR TAKING A VOLUME-ADJUSTABLE SAMPLE FROM A MOVING FLUID

FIELD OF THE INVENTION

The invention relates to apparatuses for taking a sample from a fluid moving in an open channel or flowing in an unpressurized state in a pipe, it being possible for the user of the apparatus to adjust, i.e. select, the volume of the sample.

BACKGROUND OF THE INVENTION

In the case of a conventional apparatus, the only way of adjusting the volume of the sample to be taken is for an intake/discharge pipe, which serves the purpose of fluid intake and projects into a chamber for receiving the sample, or a corresponding flexible tube, to be permanently shortened by sawing or cutting it to length, and then closed.

In the case of this conventional apparatus, therefore, the volume of the sample can be adjusted only once, specifically generally when the apparatus is first put into service. Adaptation of the volume of the sample to changing conditions is thus no longer possible during operation of the apparatus.

SUMMARY OF THE INVENTION

The invention is intended to provided a remedy to this problem.

The invention therefore provides an apparatus for taking a volume-adjustable sample from a fluid moving in an open channel or flowing in an unpressurized state in a pipe having a chamber for receiving the sample, having an intake/discharge line which is immersed in the fluid and is connected to an opening in a base of the chamber, having a sample outlet line which is arranged in the base of the chamber, having a vertical inner intake pipe, into which the intake/discharge line opens, having a rotatable outer intake pipe which is placed over the inner intake pipe, where either the wall of the inner intake pipe is provided with an axially parallel elongate hole and the wall of the outer intake pipe is provided with a helical elongate hole extending over a rotational angle of less than 360°, or is provided with a helical elongate hole extending over a rotational angle of less than 360° and the wall of the outer intake pipe is provided with an axially parallel elongate hole, and having a rotary actuator for the outer intake pipe.

According to a preferred embodiment of the invention, a crank is used as the rotary actuator for the outer intake pipe.

According to another preferred embodiment of the invention, an electronic control system for a motor for rotating the outer intake pipe is provided, into which control system data which determine the rotational angle of the outer intake pipe are to be input by the user.

According to yet another preferred embodiment of the invention, an electronic control system for a motor for rotating the outer intake pipe and a sensor arrangement are provided, which emits an analog output signal proportional to the instantaneous flow of the fluid and determining the rotational angle of the outer intake pipe.

An advantage of the invention consists in the fact that the volume of the sample to be taken can be adjusted either directly manually or electronically manually or completely electronically, that is to say as a function of a measured parameter, simply by altering the relative rotational angle between the inner and outer intake pipes.

BRIEF DESCRIPTION OF THE DRAWINGS

The invention will now be explained in more detail with reference to an exemplary embodiment of an apparatus depicted in the figures of the drawing, in which:

FIG. 2 shows the construction of the apparatus of FIG. 1, adjusted to a second predetermined, and larger volume.

DETAILED DESCRIPTION OF THE DRAWINGS

Figure 1:
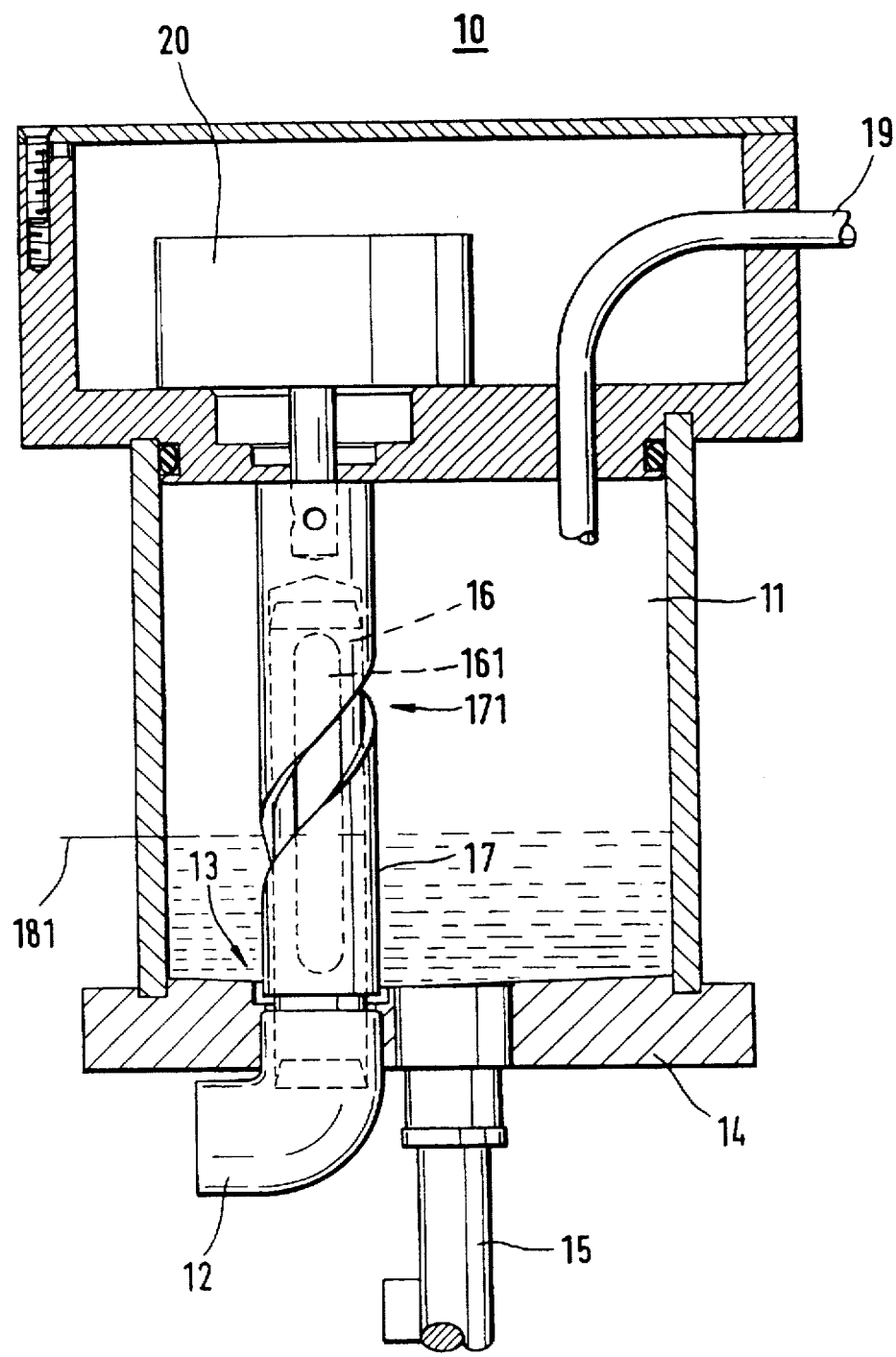
FIG. 1 diagrammatically, in section, shows the construction of an apparatus, adjusted to a first predetermined volume.

In the apparatus 10, which is shown in FIGS. 1 and 2, in each case diagrammatically, for taking a volume-adjustable sample from a fluid which is moving in an open channel or flowing in an unpressurized state in a pipe, neither of which is shown, for the sake of clarity, a chamber 11 is provided for receiving the sample.

An intake/discharge line 12, which is connected to an opening 13 in a base 14 of the chamber 11, is immersed in the fluid. Furthermore, a sample outlet line 15 is arranged in the base 14. The intake/discharge line 12 opens into a vertical inner intake pipe 16 which is arranged in the chamber 11 and over which a rotatable outer intake pipe 17 is placed.

The wall of the inner intake pipe 16 is provided with an axially parallel elongate hole 161 and the wall of the outer intake pipe 17 is provided with a helical elongate hole 171 extending over a rotational angle of less than 360°. Thus, the volume of the chamber 11 which can be filled with the fluid sample is given by the relative position of the two elongate holes 161, 171 with respect to one another, i.e. by the relative rotational angle of the outer intake pipe 17 with respect to the fixed inner intake pipe 16.

Since the lowest intersection of the two elongate holes 161, 171 is lower in FIG. 1 than in FIG. 2, which shows a different position of the elongate hole 171, the chamber 11 in FIG. 1 can only be filled up to the filling level 181, while in FIG. 2 it can be filled to the higher filling level 182.

This filling of the chamber 11 is made possible by means of an air line 19, which reaches into the chamber 11 from the top and by means of which the chamber can be exposed, on the one hand, to atmospheric pressure or, on the other hand, for example by means of a pump, to a suitable subatmospheric pressure, so that the fluid is sucked in.

After filling, for example completely, the chamber, the subatmospheric pressure is turned off again and atmospheric pressure is restored, so that the amount of fluid which is situated above the respectively set filling level, i.e. the excess amount of fluid, can flow out again via the intake/discharge line 12, and only the set volume remains in the chamber. After the excess fluid has flowed away, the set volume is drained off via the sample outlet line 15 for further use, e.g. for chemical analysis.

The above mentioned rotation of the outer intake pipe 17 can be carried out manually by the user, for example by means of a crank (not shown). However, FIGS. 1 and 2 illustrate a different, preferred manner of rotating the outer intake pipe 17, specifically by means of a motor 20, e.g. a stepper motor.

The motor 20 is allocated to an electronic control system (not shown), into which data which determine the rotational angle of the outer intake pipe are to be input by the user. Such (stepper) motor control systems are commercially available and are familiar to those skilled in the art.

It is also possible to supply the signal from a sensor arrangement (not shown) to the electronic control system, which sensor arrangement emits an analog output signal which is proportional to the instantaneous flow value of the fluid, so that the rotational angle of the outer intake pipe 17 can be adapted to this value or can track this value.

Any conventional and commercially available flow measuring arrangements may be used for this purpose. These emit an analog output signal which is proportional to the instantaneous flow, which is thus variable with time, e.g. a current signal which is in the range between 0 mA and 20 mA and is fed to the control system.

Naturally, it is also within the scope of the invention, in the context of a kinematic exchange, to fix the outer intake pipe 17 and make the inner intake pipe 16 rotatable with respect thereto, so that the relative rotational angle of the two intake pipes again determines the volume of the sample.

We claim:

1. An apparatus for taking a volume-adjustable sample from a fluid moving in an open channel or flowing in an unpressurized state in a pipe having a chamber for receiving the sample, having an intake/discharge line which is immersed in the fluid and is connected to an opening in a base of the chamber, having a sample outlet line which is arranged in the base of the chamber, having a vertical inner intake pipe, into which the intake/discharge line opens, having a rotatable outer intake pipe which is placed over the inner intake pipe, where the wall of the inner intake pipe is provided with an axially parallel elongate hole and the wall of the outer intake pipe is provided with a helical elongate hole extending over a rotational angle of less than 360°, and having a rotary actuator for the outer intake pipe.

2. The apparatus as claimed in claim 1, having a motor for rotating the outer intake pipe.

* * * * *